US011135091B2

(12) United States Patent
McCall, Jr.

(10) Patent No.: US 11,135,091 B2
(45) Date of Patent: Oct. 5, 2021

(54) DEVICE FOR OPHTHALMIC SURGERY AND METHOD OF USE THEREFOR

(71) Applicant: John A. McCall, Jr., Crockett, TX (US)

(72) Inventor: John A. McCall, Jr., Crockett, TX (US)

(*) Notice: Subject to any disclaimer, the term of this patent is extended or adjusted under 35 U.S.C. 154(b) by 123 days.

(21) Appl. No.: 16/579,258

(22) Filed: Sep. 23, 2019

(65) Prior Publication Data

US 2020/0093639 A1 Mar. 26, 2020

Related U.S. Application Data

(60) Provisional application No. 62/734,959, filed on Sep. 21, 2018.

(51) Int. Cl.
*A61F 9/008* (2006.01)
*A61F 9/009* (2006.01)

(52) U.S. Cl.
CPC .......... *A61F 9/00814* (2013.01); *A61F 9/009* (2013.01); *A61F 2009/0087* (2013.01); *A61F 2009/00868* (2013.01); *A61F 2009/00872* (2013.01); *A61F 2009/00891* (2013.01)

(58) Field of Classification Search
CPC .................. A61F 9/00814; A61F 9/009; A61F 2009/0087; A61F 2009/00868; A61F 2009/00891; A61F 2009/00872
See application file for complete search history.

(56) References Cited

U.S. PATENT DOCUMENTS 5,549,596 A * 8/1996 Latina .................... A61F 9/008
606/4
2005/0288745 A1 * 12/2005 Andersen ................. A61H 5/00
607/86

OTHER PUBLICATIONS

Latina et al. Selective Laser Trabeculoplasty Opthalmol Clin N Am 18 (2005) 409-419 (Year: 2005).*
Singh et al. "Lenses in Glaucoma" Delhi J Ophthalmol (Mar. 2018) 28 55-7 (Year: 2018).*
Ocular Instruments ("Ocular Thorpe Four Mirror Gonio Lenses" Product Data Sheet 2001 (https://ocularinc.com/products/gonio-lenses/diagnostic-gonio-lenses/ocular-thorpe-four-mirror-goniodiagnostic.html#) (Year: 2001).*
Alward "Color Atlas of Gonioscopy" The Foundation of the American Academy of Ophthalmology 1994) (Year: 1994).*
(Continued)

*Primary Examiner* — Nathan J Jenness
(74) *Attorney, Agent, or Firm* — Husch Blackwell LLP (57) ABSTRACT

A lens device for use in Selective Laser Trabeculoplasty (SLT) procedures is provided. The lens device includes four internal reflectors, each having a reflector surface configured direct a laser beam pulse toward the trabecular meshwork region of a patient's eye. Each of the four internal reflectors is arranged to correspond to a particular quadrant of the patient's eye to enable the entire 360-degrees of the trabecular meshwork to be treated with laser pulses without rotation of the lens device. A method for performing an SLT procedure using the lens device is also provided. The method includes placing the lens device of the patient's eye, aligning the internal reflectors with the quadrants of the patient's eye, directing laser pulses through each internal reflector until the trabecular meshwork in each quadrant of the patient's eye has been treated.

6 Claims, 7 Drawing Sheets

(56) References Cited

OTHER PUBLICATIONS

Volk Rapid SLT (https://www.volk.com/products/rapid-slt-slit-lamp-lens) accessed May 10, 2021 (Year: 2021).*
Latina et al. "Q-switched 532-nm Nd:YAG Laser Trabeculoplasty (Selective Laser Trabeculoplasty)" Ophthalmology. Nov. 1998; 105 (11): 2082-8) (Year: 1998).*
Alon S. "Selective Laser Trabeculoplasty: A Clinical Review." J Curr Glaucoma Pract. May-Aug. 2013; 7(2):58-65.) (Year: 2013).*
Kennedy JB et al. "Selective Laser Trabeculoplasty: An Update." Asia Pac J Ophthalmol (Phila). Jan.-Feb. 2016; 5(1):63-9. (Year: 2016).*

\* cited by examiner

DEVICE FOR OPHTHALMIC SURGERY AND METHOD OF USE THEREFOR

CROSS-REFERENCE TO RELATED APPLICATIONS

This Application claims priority to U.S. Provisional Patent Application Ser. No. 62/734,959, filed on Sep. 21, 2018, to John A. McCall, Jr., entitled "Device for Ophthalmic Surgery and Method of Use Therefor," currently pending, the entire disclosure of which is incorporated herein by reference.

BACKGROUND OF THE INVENTION

There are several therapeutic options available for treating glaucoma, including ophthalmic surgery with laser therapies, particularly for open angle glaucoma. One of these surgeries is Selective Laser Trabeculoplasty (SLT). During an SLT procedure, several selective laser shots are made to the patient's eye at even spacing to the trabecular meshwork (TM). The laser shots in the SLT procedure treat the TM with a specific wavelength light that is predominately absorbed by the melanin residing in the TM. The laser used during SLT targets only pigmented trabecular cells and intends to cause no structural or coagulative damage to the rest of the trabecular meshwork.

Safe and effective laser ophthalmic surgery requires a fine balance between the efficiency of laser shots delivered and the degree of collateral side damage. The laser-ocular tissue interaction process is reliant on three main variables, namely, wavelength, pulse duration, and deposited energy. A certain amount of energy is needed to achieve affect, while too much energy can result in unwanted collateral thermal damage.

SLT uses a Q-switched, frequency-doubled, Nd:YAG laser to selectively target the melanin-containing cells of the trabecular meshwork or selective photothermolysis. The 532 nm laser energy is delivered over a short pulse duration of three nanoseconds, which produces little collateral damage to adjacent TM. The spot size measures 400 nm. A very small amount of energy (0.6 to 0.9 mj) is applied over a relatively large area in SLT, but because the power settings are so low, there isn't enough energy to convert the electromagnetic power in the TM melanosomes into thermal energy. Only pigmented TM cells are disrupted; surrounding tissues are preserved. SLT is thought to release cytokines and other chemicals that stimulate the recruitment of macrophages, which help to phagocytize TM debris to improve outflow.

Currently, a single mirror lens is used in SLT procedures to direct the laser shots from the laser source to the TM of the patient's eye. Because the laser shots must be spread out across the TM, the lens must be rotated several times during the procedure in order to completely cover the patient's eye, which significantly reduces the overall efficiency of the procedure. Accordingly, a need exists for an improved lens device for SLT procedures and an improved method for performing SLT procedures. A need also exists for new methods for performing SLT procedures the increase accuracy, efficiency and patient comfort.

BRIEF SUMMARY OF THE INVENTION

The present invention is directed generally to a four-mirror lens device used in connection with Selective Laser Trabeculoplasty (SLT) procedures for treating glaucoma or other issues in a patient's eye. The lens device can include an outer body having a first end for receiving laser beam pulses from a laser source during a SLT procedure. The outer body can also include a second end for being placed on the patient's eye during the SLT procedure. The second end can allow the laser pulses received through the first end to be transmitted to the patient's eye.

Located within the interior of the lens device can be four internal reflectors. Each internal reflector can include a mirrored or reflective surface that is configured to direct light or laser pulses to a particular quadrant of the patient's eye, and particularly, the trabecular meshwork located within that quadrant. Because of the arrangement of the four internal reflectors, when the lens device is positioned on a patient's eye, nearly the entire 360-degrees of the trabecular meshwork around the patient's eye is visible simultaneously. This can enable an operator to perform an SLT procedure and transmit laser pulses through each internal reflector to cover the entirety of the trabecular meshwork without any rotation of the lens device.

The present invention is further directed to a modified method for performing a Selective Laser Trabeculoplasty (SLT) procedure to treat glaucoma or other issues in a patient's eye using a traditional single-mirror lens device. The modified method utilizes a quadrant approach rather than a continuous rotation approach to treat the entire 360-degrees of the trabecular meshwork with laser beam pulses. The modified method begins by orientating the single-mirror lens device to view a center-line of a first quadrant of the patient's eye. The operator may then transmit laser pulses to trabecular meshwork within the first quadrant by starting at the center-line and moving in the clockwise direction until the edge of the field of view is reached. The operator may then return to the center-line of the quadrant and continue to transmit laser pulses while moving in the counter-clockwise direction until the edge of the field of view is reached. The lens device may be rotated 180-degrees and these steps can be repeated for a second quadrant. The lens device may then be rotated 90-degrees and the steps repeated for a third quadrant. The lens device may then be rotated 180-degrees again the steps repeated for a fourth quadrant.

The present invention is further directed to a method for performing a Selective Laser Trabeculoplasty (SLT) procedure to treat glaucoma or other issues in a patient's eye using the four-mirror lens device of the present invention. This method allows for the treatment of the entire 360-degrees of the trabecular meshwork of a patient's eye without any rotation of the lens device during the SLT procedure. The method can include the steps of:

(i) providing a lens device having four internal reflectors, each internal reflector configured to direct transmitted laser beam pulses to a particular quadrant of said patient's eye;

(ii) positioning said lens device onto said patient's eye;

(iii) aligning said four internal reflectors of said lens device with the four quadrants of said patient's eye;

(iv) directing said laser emitter to the internal reflector corresponding to a first quadrant of said patient's eye and transmitting laser beam pulses to through said internal reflector to treat the trabecular meshwork located within said first quadrant;

(v) directing said laser emitter to the internal reflector corresponding to a second quadrant of said patient's eye and transmitting laser beam pulses to through said internal reflector to treat the trabecular meshwork located within said second quadrant;

(vi) directing said laser emitter to the internal reflector corresponding to third quadrant of said patient's eye and transmitting laser beam pulses to through said internal reflector to treat the trabecular meshwork located within said third quadrant; and (vii) directing said laser emitter to the internal reflector corresponding to a fourth quadrant of said patient's eye and transmitting laser beam pulses to through said internal reflector to treat the trabecular meshwork located within said fourth quadrant.

Other aspects and advantages of the present invention will be apparent from the following detailed description of the preferred embodiments of the accompanying drawing figures.

DESCRIPTION OF THE SEVERAL VIEWS OF THE DRAWING

In the accompanying drawing, which forms a part of the specification and is to be read in conjunction therewith in which like reference numerals are used to indicate like or similar parts in the various views.

DETAILED DESCRIPTION OF THE INVENTION

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

The following detailed description of the invention references specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

The present invention is directed to an ophthalmic lens device 10 used during a Selective Laser Trabeculoplasty (SLT) procedure to direct laser energy pulses to the trabecular meshwork (TM) portion of a patient's eye to treat glaucoma or other issues. As described below, the present invention is also directed to a method 100 for performing a SLT procedure using a traditional single-mirror lens device and a method 200 for performing an SLT procedure using lens device 10 of the present invention.

Figure 1:
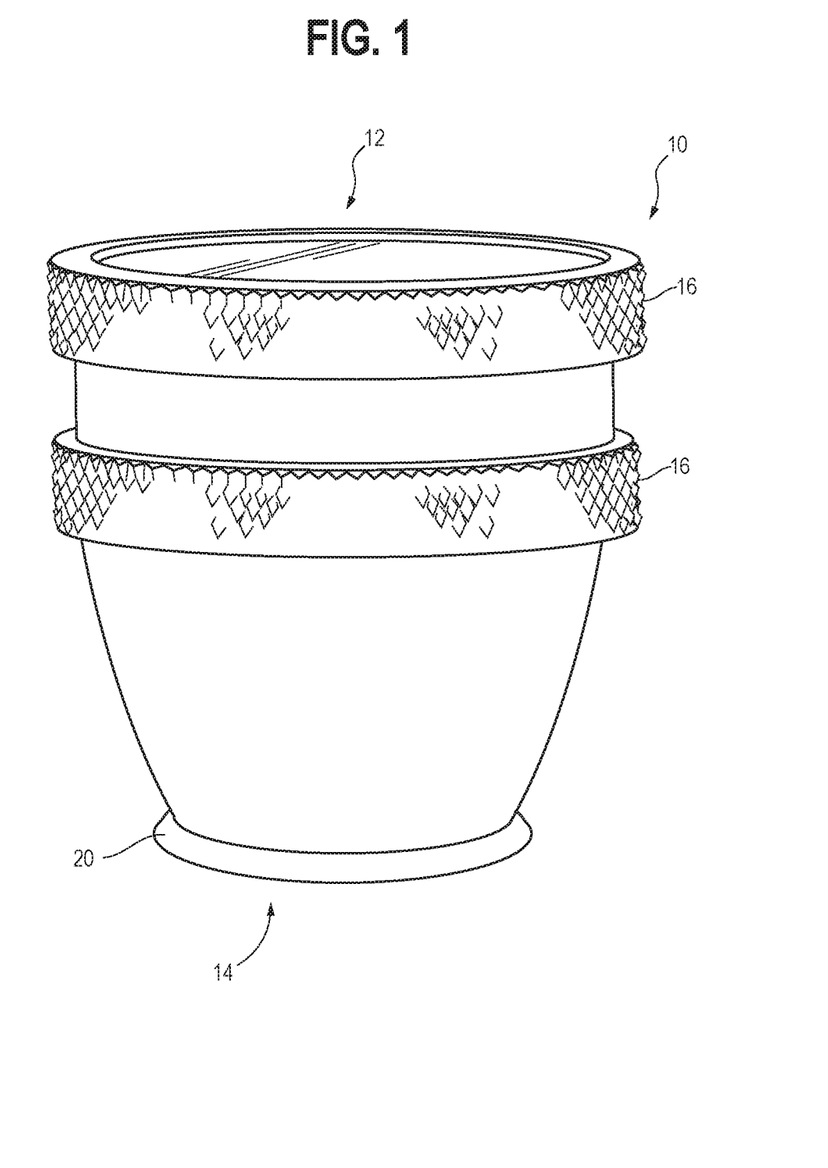
FIG. 1 is a side perspective view of a four-mirror lens device for use in Selective Laser Trabeculoplasty procedures in accordance with one embodiment of the present invention.
Figure 2:
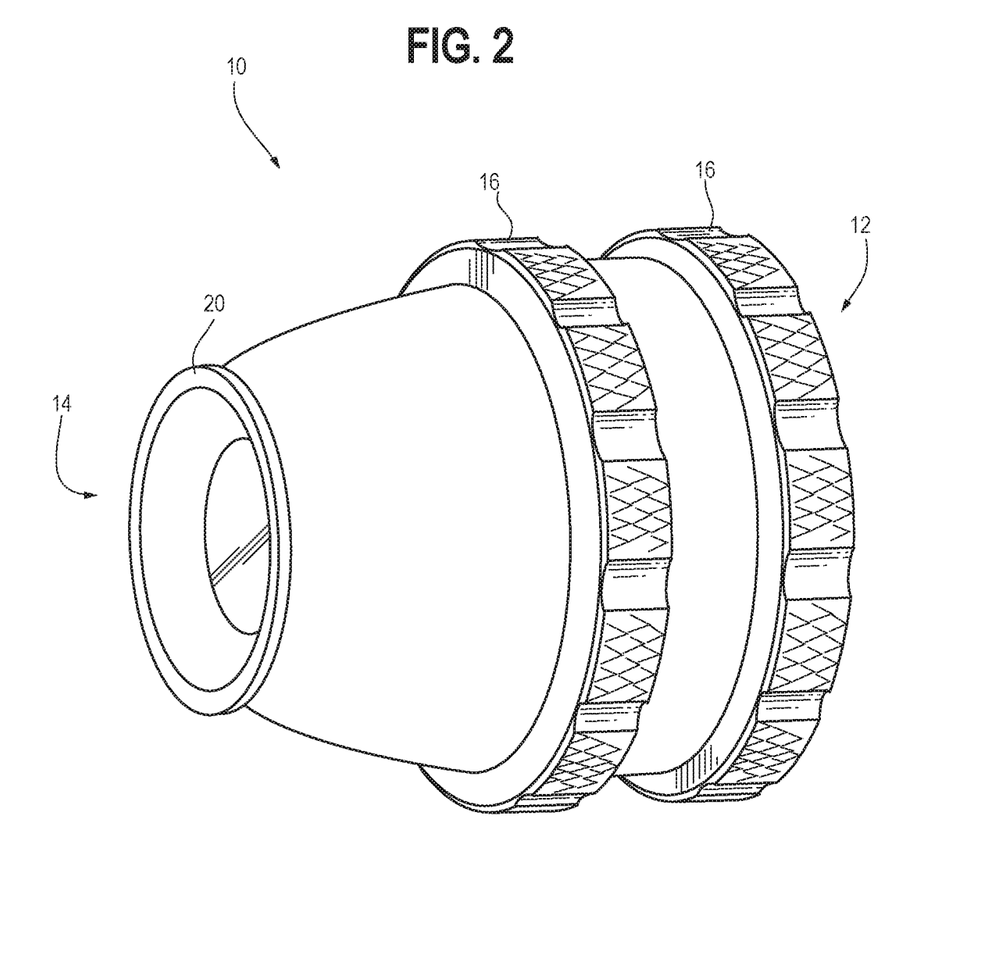
FIG. 2 is a rear perspective view of a four-mirror lens device for use in Selective Laser Trabeculoplasty procedures in accordance with one embodiment of the present invention.
Figure 3:
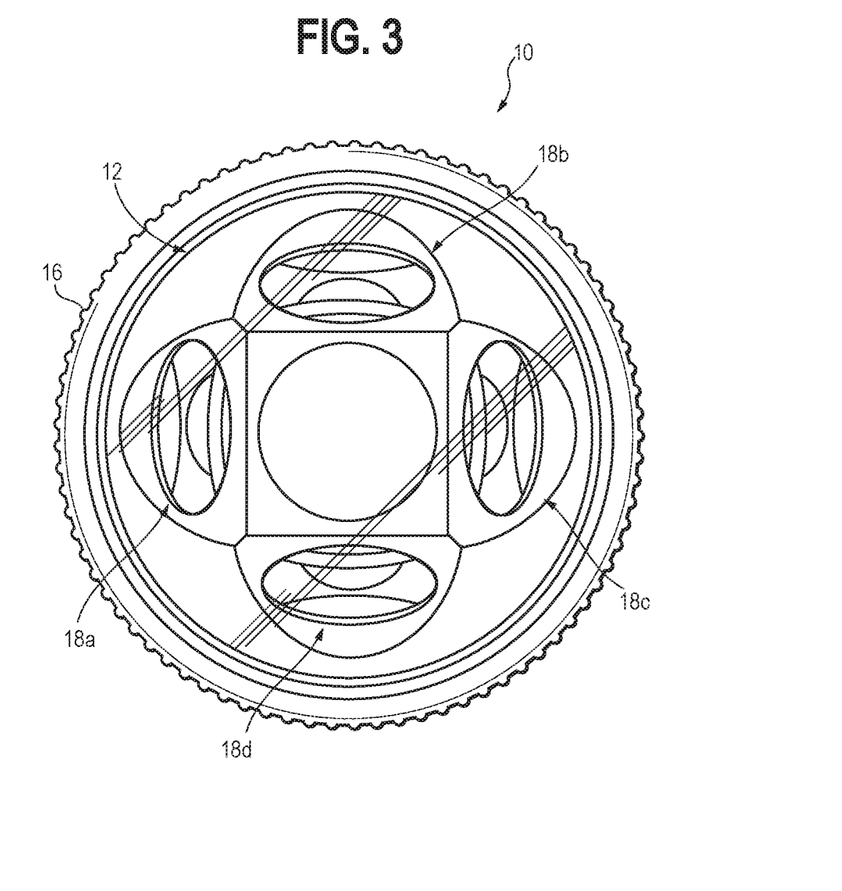
FIG. 3 is a top plan view of a four-mirror lens device for use in Selective Laser Trabeculoplasty procedures in accordance with one embodiment of the present invention.

As best shown in FIGS. 1-3, lens device 10 can be constructed with an exterior design and configuration similar to SLT lens devices currently known and utilized in the industry. Such prior art lens devices include the Volk® single-mirror SLT lens and the Ocular® Latina SLT Gonio laser lens, the structure, design and configuration of which are incorporated herein by reference. As shown in FIGS. 1-3, lens device 10 can include an outer body portion with a laser light beam receiving end 12 for receiving laser pulses from a laser source or emitter, and a patient contact end 14. As best shown in FIG. 2, patient contact end 14 may include a curved surface so that contact end 14 may be fitted onto the patient's cornea during an SLT procedure. The patient contact end 14 may also be configured to receive the laser pulses passing through the interior of the device and allow the re-directed laser pulses to be transmitted to the patient's eye.

Lens device 10 may further include gripping and adjustment means 16 provided around the exterior perimeter of lens device 10 configured to assist a user in holding and adjusting lens device 10 during a SLT procedure. As illustrated in FIG. 1, gripping and adjustment means 16 may include a plurality of ridges formed onto the surface of device 10. As illustrated in FIG. 2, gripping and adjustment means may also or alternatively include a plurality of indentations of grooves formed into the surface of device 10. Any other suitable means for facilitating increased grip may also be used.

As further shown in FIGS. 1 and 2, the patient contact end 14 can include a modified flange 20 that can be larger than a standard lens flange and can (a) keep the lens in place and stable throughout the SLT procedure and (b) can keep any excess pressure from the surgeons hand from distorting the view by wrinkling the cornea.

As best shown in FIG. 3, located within lens device 10 can be four internal reflective surfaces 18a, 18b, 18c, and 18d configured as mirrors or reflectors. Reflectors 18a-18d can be configured in a manner similar to the single large reflective facet provided in traditional single-mirror SLT lenses, such as the Volk® or Ocular® lenses identified above. Reflectors 18a-18d can further provide simultaneous views of the trabecular meshwork (TM) and iridocorneal angle of a patient's eye when placed thereon (see FIG. 4).

Each of the four reflectors 18a-18d can be configured to direct the light laser beams utilized during an SLT procedure to a specific portion of the patient's eye and specifically the trabecular meshwork (TM) of the patient's eye, which as described in greater detail below, can greatly increase the precision and efficiency of the SLT procedure. According to one embodiment, when in use, the lens device 10 can be configured so that each reflector 18a-d corresponds to particular quadrant of the user's eye (i.e., superior, inferior, left and right quadrants). Each reflector 18a-18d has a specific direction and/or curvature that enables light/energy directed through the receiving end 12 of lens device 10 to be redirected to the trabecular meshwork region of the patient's eye within a particular quadrant of the patient's eye. The four reflectors 18a-18d are further selectively arranged so collectively, the reflectors 18a-18d cover the entirety of the patient's eye.

Figure 4:
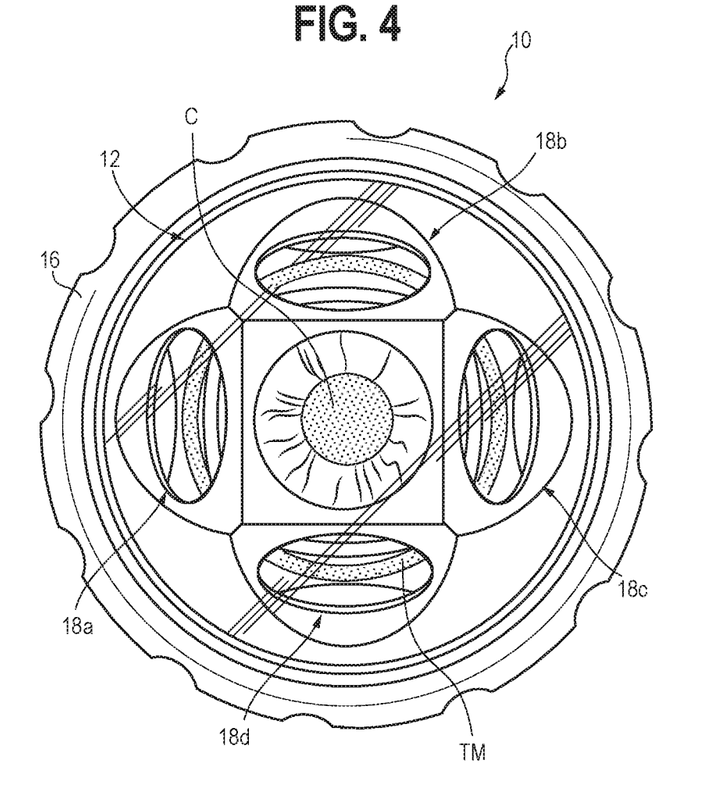
FIG. 4 is a top plan view of a four-mirror lens device for use in Selective Laser Trabeculoplasty procedures, illustrating the device when placed on a patient's eye in accordance with one embodiment of the present invention.

For purposes of example, as shown in FIGS. 3 and 4, according to one embodiment reflector 18a may be positioned in the left quadrant within the interior of lens device 10, reflector 18b may be positioned in the superior (upper) quadrant, reflector 18c may be positioned in the right quadrant, and reflector 18d may be positioned in the inferior (lower) quadrant. As shown in FIGS. 3 and 4, the reflectors 18a-18d may be sized and arranged within the interior of lens device 10 so that they collectively provide a near 360-degree view of the trabecular meshwork and iridocorneal angle with clear and accurate imaging.

According to one embodiment, reflectors 18a-18d can be configured with total internal reflection or almost total internal reflection in order to reduce the energy loss of the laser light beam after reflection off of the reflector 18a-d. Lens device 10 can also be configured in certain embodiments to allow for magnification of the laser light beam in order to account for the slight loss in energy from a result of the reflectors 18a-d. According to one embodiment, each reflector 18a-18d can be configured to provide a magnification of approximately 1.0 across each reflector to maintain a consistent laser beam sport size and power density. In certain alternative select embodiments, the magnification can be along the order of 1.1 to 1.25; however, it is recognized that any desired magnification (including no magnification) can be utilized in various embodiments of the present invention.

FIG. 4 provides a schematic representation of lens device 10 in use with a patient in accordance with one embodiment of the present invention. As shown in FIG. 4, when patient contact end 14 of device 10 is seated on the cornea C of a patient's eye, the four individual reflectors 18a-18d enable simultaneous viewing of the trabecular meshwork TM in each quadrant of the patient's eye. As a result of the four distinct reflectors 18a-18d, an operator may simultaneously view approximately the entire 360-degrees of the trabecular meshwork of the patient's eye without any rotation of the lens device 10.

Figure 5:
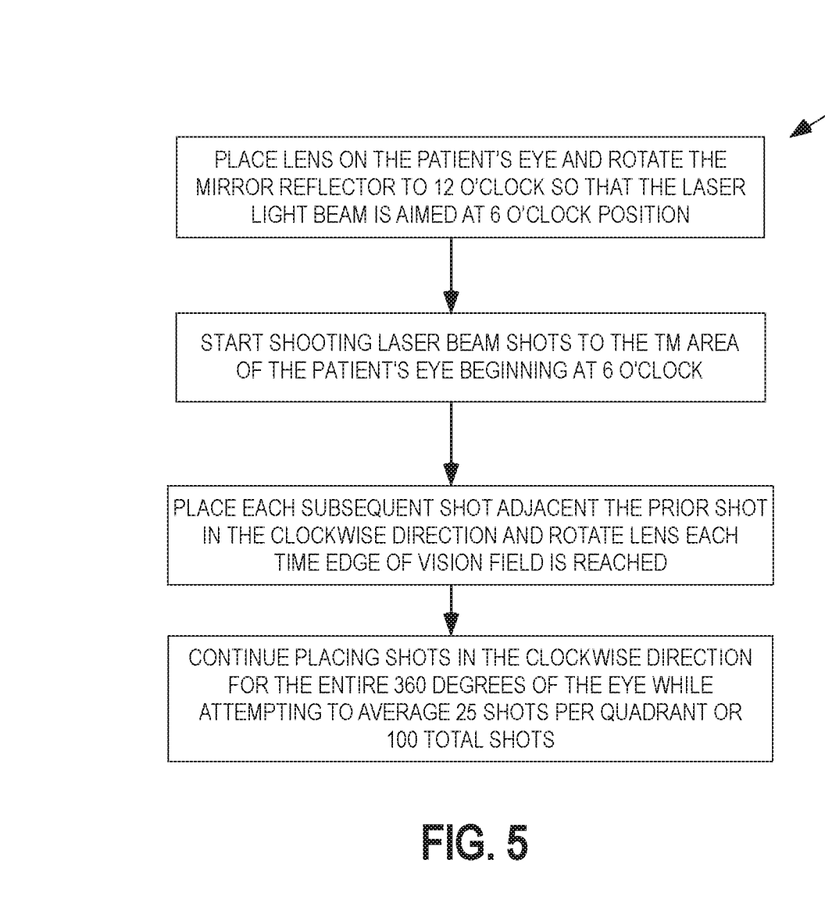
FIG. 5 is a flow chart of a prior art method for performing a Selective Laser Trabeculoplasty procedure with a single-mirror lens device as currently known in the industry.
Figure 5A:
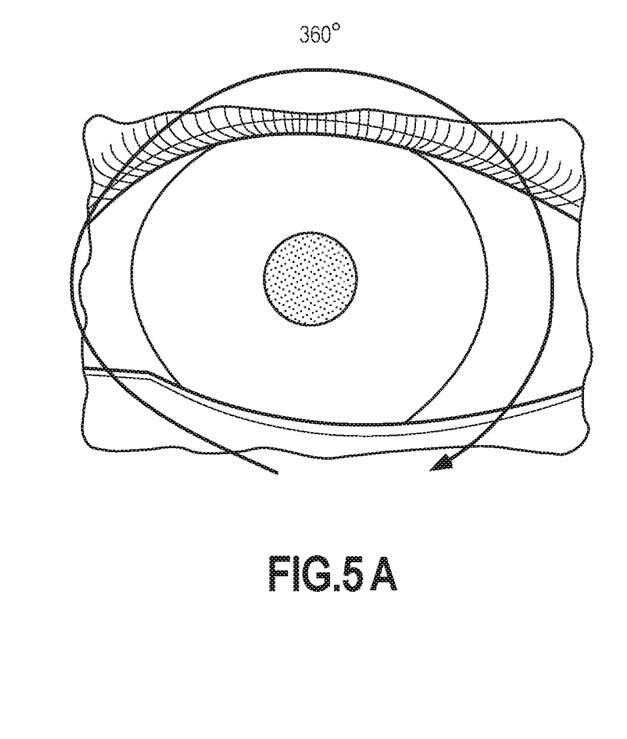
FIG. 5A is a schematic diagram of the prior art method of FIG. 5.

FIGS. 5 and 5A illustrate the currently utilized method for performing a Selective Laser Trabeculoplasty (SLT) procedure to treat glaucoma in a patient's eye as commonly known in the prior art. This method uses a laser energy emitter source to shoot bursts of laser pulses or shots to the trabecular meshwork portion of the patient's eye using a single-mirror lens device, such as the Volk® or Ocular® lenses identified above. The eye is treated with a numbing substance and the eye receiving end of the single-mirror lens device is positioned onto the cornea of the patient's eye. The single-mirror lens device is then utilized to reflect laser beam pulses across the iris of the patient's eye and into the trabecular meshwork area to be treated.

As illustrated in FIGS. 5 and 5A, this prior art method begins with the operating doctor or technician orientating the lens device to the 12 o'clock (i.e., upper vertical) position so that the laser beam pulses emitted from the laser energy source will reflect off the single-mirror reflector toward the 6 o'clock (i.e., lower vertical) position of the patient's eye, and specifically the trabecular meshwork area of the eye. The operator begins transmitting laser beam pulses into the single-mirror lens device, starting at the 6 o'clock position of the trabecular meshwork of the patient's eye and continuing in the clockwise direction (as demonstrated by FIG. 5A). The operator continues to transmit laser beam shots through the single-mirror lens device and into the trabecular meshwork of the patient's eye in a clockwise direction around the trabecular meshwork until the edge of the field of vision of the lens device is reached. Once the edge of the field of vision is reached, the operator must rotate the lens device in a clockwise direction to replace the operator's field of vision through the lens device with a new area of the trabecular meshwork that has not yet been treated. After rotating the lens device to the new field of vision, the operator resumes transmitting laser beam shots to the trabecular meshwork area of the patient's eye in a clockwise direction until the operator's field of vision is again reached. The operator must then rotate the lens device clockwise again and repeat the prior process until the operator has completed an entire 360-degree rotation to treat the entire trabecular meshwork of the patient's eye.

This current prior art method provides several difficulties and inefficiencies during a SLT procedure. First, it is easy for the operator to get lost in terms of location or direction, particularly during and after a rotation of the lens device, which results in unnecessary overlapping of laser beam shots in the same location of the trabecular meshwork area of the patient's eye. Typically, this method requires approximately 100 laser beam shots with about 25 shots per quadrant of the patient's eye, with some of the laser beam shots being applied to the same area of the trabecular meshwork due to inaccurate rotation of the lens device. Second, the operator must balance rotating the lens device while simultaneously stabilizing the lens device firmly on the cornea, this can increase the time duration of the overall procedure and can cause discomfort and irritation for the patient. Particularly, significant rotation of the lens device when seated on the patient's cornea can lead to the patient shifting his or her eye, blinking or otherwise disrupting the positioning of the lens device.

Figure 6:
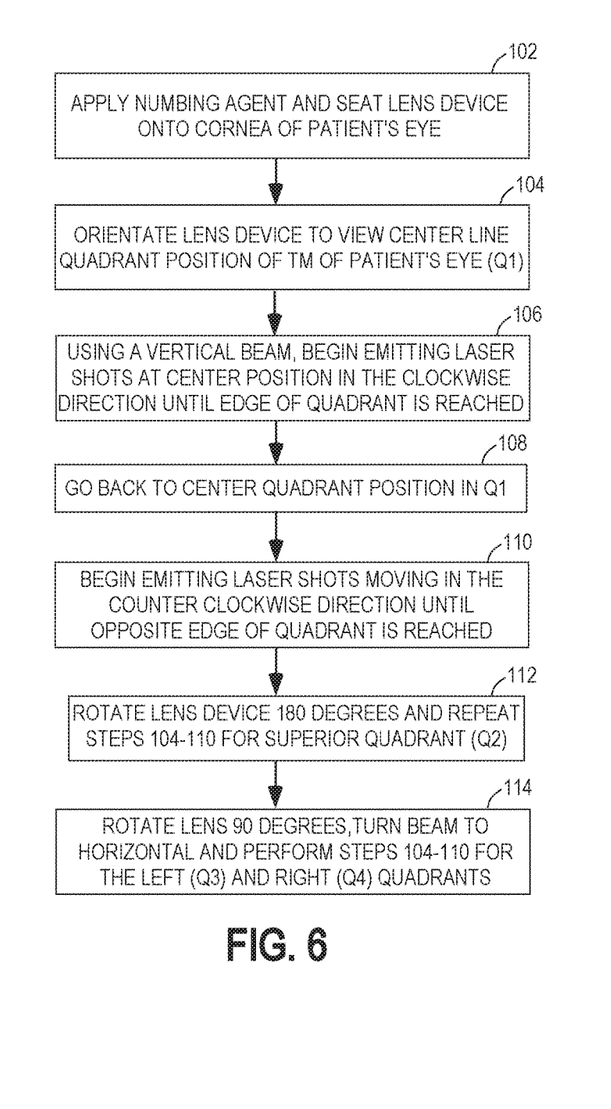
FIG. 6 is a flow chart of a modified method for performing a Selective Laser Trabeculoplasty procedure with a single-mirror lens device in accordance with one embodiment of the present invention.
Figure 6A:
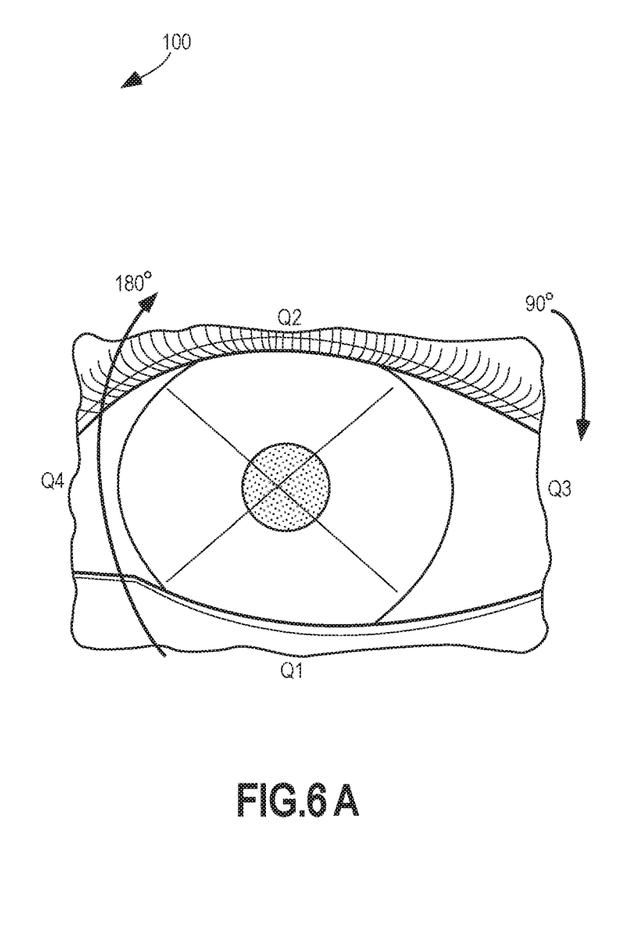
FIG. 6A is a schematic diagram of the modified method of FIG. 6 in accordance with one embodiment of the present invention.

FIGS. 6 and 6A illustrate a modified method 100 for performing an SLT procedure to treat glaucoma in a patient's eye using a single-mirror lens device (such as the Volk® or Ocular® lenses identified above) in accordance with one embodiment of the present invention. Method 100 uses a laser energy emitter source to shoot bursts of laser pulses or shots to the trabecular meshwork portion of the patient's eye through the single-mirror lens device in the manner currently utilized during SLT procedures and described above. However, as best illustrated in FIGS. 6 and 6A, through method 100, the operator performs the SLT procedure in accordance with quadrants which reduces the total rotational requirements of the lens device during the procedure.

Method 100 begins by at step 102 where the patient's eye may be treated with a numbing substance and the eye receiving end of the single-mirror lens device may be positioned onto the cornea of the patient's eye. The single-mirror lens device is then utilized to reflect laser beam pulses across the iris of the patient's eye and into the trabecular meshwork area to be treated in accordance with steps 104-114 described below. At step 104, the operator orientates the lens device so that the laser beam pulses transmitted from the laser source will reflect off the single-mirror reflector toward the 6 o'clock center-line position of the patient's eye, and specifically the trabecular meshwork area of the eye. As best illustrated in FIG. 6A, the 6 o'clock center-line position can represent the vertical center of the inferior (lower) quadrant designated as Q1.

Next at step 106, the operator may begin transmitting laser beam shots (using a vertical beam) from the laser source directly at the 6 o'clock center position and move in the clockwise direction around the trabecular meshwork while transmitting intermittent laser shots. The operator will continue to travel around the trabecular meshwork in the clockwise direction transmitting laser shots until the edge of the field of vision is reached, which corresponds to the left edge of quadrant Q1. The operator may then cease transmitting laser shots, and then at step 108, redirect the laser emitter source back to the 6 o'clock center position in quadrant Q1. Next at step 110, the operator may begin transmitting laser beam shots from the laser emitter source directly at the 6 o'clock center position and move in the counterclockwise direction around the trabecular meshwork while transmitting intermittent laser shots. During step 110, the operator may continue to travel around the trabecular meshwork in the counterclockwise direction transmitting laser shots until the edge of the field of vision is reached, which corresponds to the right edge of quadrant Q1. The operator may then cease transmitting laser shots and proceed to step 112.

At step 112, the operator may rotate the lens device 180 degrees so that the laser beam pulses emitted from the laser emitter source will reflect off the single-mirror reflector of the lens device toward the 12 o'clock center-line position of the patient's eye. The operator may then repeat steps 104-110 for the superior (upper) quadrant of the patient's eye, designated as Q2 in FIG. 6A. The operator may begin at the 12 o'clock (center) position of quadrant Q2 and transmit laser beam shots to the trabecular meshwork while moving in the clockwise direction until the edge of the field of vision is reached, which corresponds to the right edge of quadrant Q2. The operator may then cease transmitting laser shots and re-orientate back to the 12 o'clock (center) position of Q2 and then being transmitting laser shots around the trabecular meshwork in the counterclockwise direction until the edge of the field of vision is reached, which corresponds to the left edge of quadrant Q2. The operator may then cease transmitting laser shots and proceed to step 114.

At step 114, the operator may rotate the lens device 90 degrees so that the laser beam pulses emitted from the laser emitter source will reflect off the single-mirror reflector toward the 3 o'clock center-line position of the patient's eye. The operator may then turn the laser beam horizontal and carry out steps 104-110 for the right quadrant of the patient's eye, designated as Q3 in FIG. 6A. The operator may begin at the 3 o'clock (center) position of quadrant Q3 and transmit laser beam shots to the trabecular meshwork while moving in the clockwise direction until the edge of the field of vision is reached, which corresponds to the lower edge of quadrant Q3. The operator may then cease transmitting laser shots and re-orientate back to the 3 o'clock (center) position of Q3 and then being transmitting laser shots around the trabecular meshwork in the counterclockwise direction until the edge of the field of vision is reached, which corresponds to the upper edge of quadrant Q3.

The operator may then cease transmitting laser shots and rotate the lens device 180 degrees so that the laser beam pulses emitted from the laser emitter source will reflect off the single-mirror reflector toward the 9 o'clock center position of the patient's eye. The operator may then carry out steps 104-110 for the left quadrant of the patient's eye, designated as Q4 in FIG. 6A. The operator may begin at the 9 o'clock (center) position of quadrant Q4 and transmit laser beam shots to the trabecular meshwork while moving in the clockwise direction until the edge of the field of vision is reached, which corresponds to the upper edge of quadrant Q4. The operator may then cease transmitting laser shots and re-orientate back to the 9 o'clock (center) position of Q4 and then being transmitting laser shots around the trabecular meshwork in the counterclockwise direction until the edge of the field of vision is reached, which corresponds to the lower edge of quadrant Q4.

Using method 100 described above allows the operator to cover the entire 360-degree area of the trabecular meshwork during the SLT procedure by using four individual calculated rotations of the lens device as opposed to a continuous 360-degree rotation. This can enable the operator to increase accuracy and efficiency, minimize overlapping of laser shots to the same trabecular meshwork area and reduce the total time for the SLT procedure.

It is also recognized that method 100 may be performed by completing the four quadrants (Q1-Q4) of the patient's eye in any desired order. For example, the steps 104-110 may be performed for Q1 first, Q4 second, Q2 third, and finally Q3 fourth, each time rotating the lens device 90 degrees.

Figure 7:
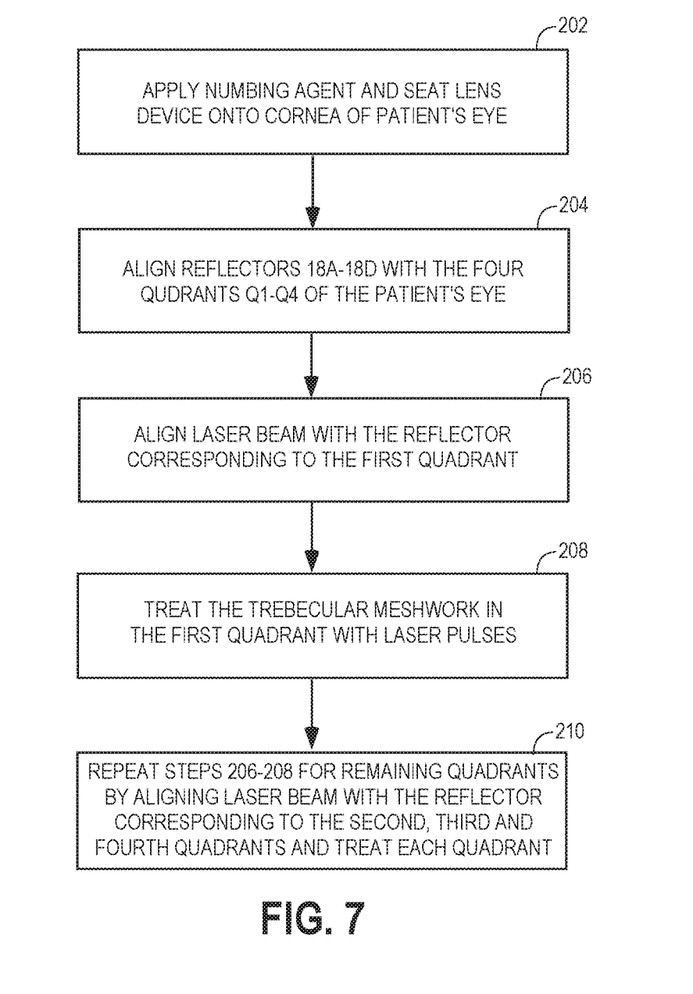
FIG. 7 is a flow chart of a method for performing a Selective Laser Trabeculoplasty procedure with a four-mirror lens device in accordance with one embodiment of the present invention.
Figure 7A:
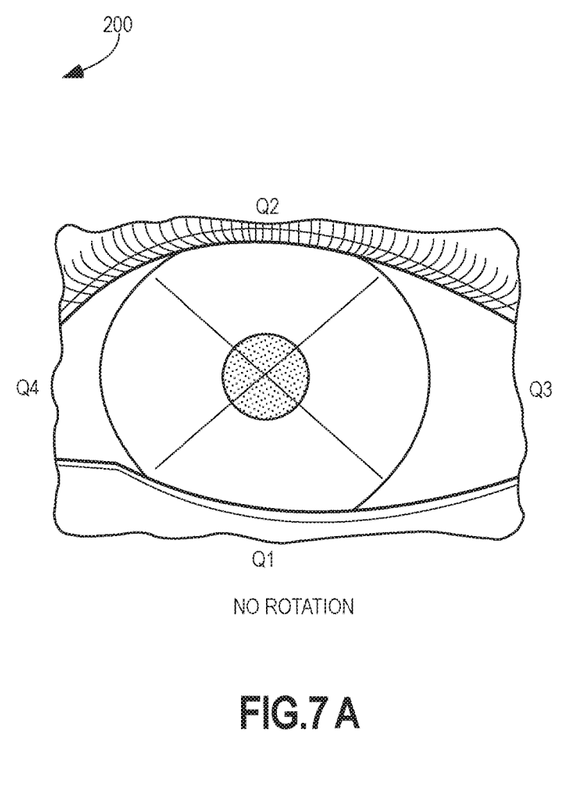
FIG. 7A is a schematic diagram of the method of FIG. 7 in accordance with one embodiment of the present invention.

While method 100 described above increases the accuracy and efficiency of an SLT procedure using a single-mirror lens device, it still requires rotation of the lens device during the SLT procedure to cover the entire 360-degree area of the trabecular meshwork, which can impact efficiency and patient comfort. FIGS. 7 and 7A illustrate a method 200 that may be used in connection with the four-mirror lens device 10 of the present invention to perform an SLT procedure without any rotation of the lens device 10 to cover the entire 360-degree area of the trabecular meshwork. As described above, and best illustrated in FIG. 4, the four individual reflectors 18a-18d arranged within the four different quadrants of the interior of lens device 10 collectively provide a near 360-degree view of the trabecular meshwork and iridocorneal angle with clear and accurate imaging. As a result, an SLT procedure may be completed using lens device 10 without any rotation of lens device 10 during the procedure as described below.

Method 200 utilizes lens device 10 of the present invention in connection with a standard laser energy emitter source to shoot bursts of laser pulses or shots to the trabecular meshwork portion of the patient's eye. As illustrated in FIG. 7, method 200 can begin at step 202 where the patient's eye is treated with a numbing substance and the eye receiving end 14 of lens device 10 is positioned onto the cornea of the patient's eye. Next, at step 204, the operator may align reflectors 18a-18d of lens device 10 with the four quadrants of the patient's eye (Q1-Q4 as depicted in FIG. 7A) so that a near 360-degree view of the trabecular meshwork of the patient's eye is visible.

Next at step 206, the operator may align the laser energy source with the reflector 18 corresponding to quadrant Q1 to shoot laser beam pulses to the trabecular meshwork within Q1 and visible through the reflector 18. At step 208, the operator may treat the trabecular meshwork within quadrant Q1 by transmitting laser beam pulses to the trabecular meshwork. During step 208, the operator may begin at one edge of quadrant Q1 and move in the clockwise or counterclockwise direction to the opposing edge of the quadrant while transmitting intermittent laser beam pulses to treat the entire area of the trabecular meshwork visible in the quadrant through reflector 18. Alternatively, the operator may treat the trabecular meshwork visible in the quadrant in any suitable manner.

Next at step 210, the operator may repeat steps 206 and 208 for each of the remaining quadrants Q2-Q4 in order to treat the entire 360-degree area of the patient's eye with laser beam pulses. For example, following quadrant Q1, the operator may align the laser energy source with the reflector 18 corresponding to quadrant Q2 and transmit laser beam pulses across the entire visible area of the trabecular meshwork within quadrant Q2, then align the laser energy source with the reflector 18 corresponding to quadrant Q3 and transmit laser beam pulses across the entire visible area of the trabecular meshwork within quadrant Q3, and then finally align the laser energy source with the reflector 18 corresponding to quadrant Q4 and transmit laser beam pulses across the entire visible area of the trabecular meshwork within quadrant Q4. The operator may also treat each quadrant Q1-Q4 using steps 206 and 208 in any desired order.

Because there is no rotation required using method 200 and lens device 10, there is very limited overlap and excess shots made to the patient's trabecular meshwork during the SLT procedure. This greatly increases the efficiency of the procedure and reduces the total amount of energy expended during the procedure. In addition, method 200 enables the SLT procedure to be completed at a rate of approximately 2.5 minutes per eye (as opposed to a standard 7-8 minutes per eye using a single-mirror lens device).

From the foregoing, it will be seen that this invention is one well adapted to attain all the ends and objects hereinabove set forth together with other advantages which are obvious and which are inherent to the structure. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A method for performing a selective laser trabeculoplasty (SLT) procedure using a laser source to transmit laser beam pulses to a trabecular meshwork of a patient's eye, said method comprising the steps of:
    providing a lens device having four internal reflectors, each internal reflector configured to direct transmitted laser beam pulses to a particular quadrant of said patient's eye;
    positioning said lens device onto said patient's eye;
    aligning said four internal reflectors of said lens device with the four quadrants of said patient's eye;
    directing said laser source to the internal reflector corresponding to a first quadrant of said patient's eye and transmitting laser beam pulses through a first of said internal reflectors to treat the trabecular meshwork located within said first quadrant;
    directing said laser source to the internal reflector corresponding to a second quadrant of said patient's eye and transmitting laser beam pulses through a second of said internal reflectors to treat the trabecular meshwork located within said second quadrant;
    directing said laser source to the internal reflector corresponding to third quadrant of said patient's eye and transmitting laser beam pulses through a third of said internal reflectors to treat the trabecular meshwork located within said third quadrant; and
    directing said laser source to the internal reflector corresponding to a fourth quadrant of said patient's eye and transmitting laser beam pulses through a fourth of said internal reflectors to treat the trabecular meshwork located within said fourth quadrant.

2. The method of claim 1, wherein the steps of directing said laser source to said internal reflectors corresponding to said first, second, third and fourth quadrants of said patient's eye does not include any rotation of said lens device.

3. The method of claim 1, wherein transmission of said laser beam pulses through each of said internal reflectors to said first, second, third, and fourth quadrants of said patient's eye enables treatment of 360-degrees of the trabecular meshwork of said patient's eye without rotation of said lens device.

4. The method of claim 1, wherein said laser source is moved in a clockwise direction when transmitting said beam pulses through said internal reflectors.

5. The method of claim 1, wherein said first quadrant is the inferior quadrant of said patient's eye, said second quadrant is the superior quadrant of said patient's eye, said third quadrant is the right quadrant of said patient's eye, and thesaid fourth quadrant is the left quadrant of said patient's eye.

6. The method of claim 1, wherein said lens device comprises:
    a device body having a first end configured to receive a laser beam pulse transmission, a second end configured for placement on a patient's eye, and an interior positioned therebetween;
    wherein said four internal reflectors are located within said interior of said lens device.

\* \* \* \* \*

UNITED STATES PATENT AND TRADEMARK OFFICE
CERTIFICATE OF CORRECTION

| | |
|---|---|
| PATENT NO. | : 11,135,091 B2 |
| APPLICATION NO. | : 16/579258 |
| DATED | : October 5, 2021 |
| INVENTOR(S) | : John A. McCall, Jr. |

It is certified that error appears in the above-identified patent and that said Letters Patent is hereby corrected as shown below:

On the Title Page

Item (57) Abstract, Line 4, before "direct", insert -- to --
Item (57) Abstract, Line 11, delete "of" and insert -- on --
Item (57) Abstract, Line 13, after "eye,", insert -- and --

In the Specification

Column 1, Line 6, delete "the" and insert -- to --
Column 2, Line 3, delete second occurrence of "a" and insert -- an --
Column 2, Line 42, delete "again" and insert -- and --
Column 2, Line 60, delete "to"
Column 2, Line 65, delete "to"
Column 3, Line 3, delete "to"
Column 3, Line 8, delete "to"
Column 4, Line 17, delete second occurrence of "a" and insert -- an --
Column 4, Line 41, delete "a" and insert -- an --
Column 4, Line 52, delete "can"
Column 5, Line 4, delete "18a-d" and insert -- 18a-18d --
Column 5, Line 4, after "corresponds to", insert -- a --
Column 5, Line 5, after "left", insert a -- , --
Column 5, Line 11, after "so", insert a -- , --
Column 5, Line 15, after "embodiment", insert a -- , --
Column 5, Line 28, delete "18a-d" and insert -- 18a-18d --
Column 5, Line 32, delete "18a-d" and insert -- 18a-18d --
Column 5, Line 35, delete "sport" and insert -- shot --
Column 6, Line 27, delete "a" and insert -- an --
Column 6, Line 29, delete "this" and insert -- which --
Column 6, Line 59, delete "by"
Column 7, Line 42, delete "being" and insert -- begin --

Signed and Sealed this
Third Day of May, 2022

*Katherine Kelly Vidal*
Katherine Kelly Vidal
*Director of the United States Patent and Trademark Office*

CERTIFICATE OF CORRECTION (continued)
U.S. Pat. No. 11,135,091 B2

Column 7, Line 60, delete "being" and insert -- begin --
Column 8, Line 10, delete "being" and insert -- begin --
Column 8, Line 24, delete "the"

In the Claims

Column 10, Claim 1, Line 25, before "third", insert -- a --
Column 10, Claim 5, Line 52, delete "thesaid" and insert -- said --